US011007071B2

(12) United States Patent
Guo et al.

(10) Patent No.: US 11,007,071 B2
(45) Date of Patent: May 18, 2021

(54) ARTIFICIAL LIMB

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Shaofei Guo, Beijing (CN); Zhonghua Li, Beijing (CN); Jian Sang, Beijing (CN); Shipeng Wang, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 146 days.

(21) Appl. No.: 16/400,184

(22) Filed: May 1, 2019

(65) Prior Publication Data

US 2020/0069439 A1 Mar. 5, 2020

(30) Foreign Application Priority Data

Aug. 30, 2018 (CN) .......................... 201811005799.8

(51) Int. Cl.
*A61F 2/58* (2006.01)
*A61F 2/72* (2006.01)
(Continued)

(52) U.S. Cl.
CPC ................ *A61F 2/586* (2013.01); *A61F 2/72* (2013.01); *A61F 2002/5007* (2013.01); (Continued)

(58) Field of Classification Search
CPC .. A61F 2/586; A61F 2/72; A61F 2/585; A61F 2002/5007; A61F 2002/5038;
(Continued)

(56) References Cited

U.S. PATENT DOCUMENTS

| 6,896,704 B1* | 5/2005 | Higuchi ..................... A61F 2/68 623/64 |
| 2011/0160873 A1* | 6/2011 | Jaworski .................. A61F 2/586 623/64 |

(Continued)

FOREIGN PATENT DOCUMENTS

| CN | 201160923 | 12/2008 |
| CN | 101836908 A | 9/2010 |

(Continued)

OTHER PUBLICATIONS

Chinese Office Action dated Mar. 2, 2020 corresponding to Chinese Patent Application No. 2018110057998; 35 pages.

*Primary Examiner* — Suba Ganesan
*Assistant Examiner* — Aren Patel
(74) *Attorney, Agent, or Firm* — Leason Ellis LLP

(57) ABSTRACT

An artificial limb. The artificial includes a finger part and a drive unit for the finger part. The drive unit includes: a drive output part, a movable part and a drive rope. The movable part is configured to be connected with the drive output part and is capable of moving under a drive of the drive output part. The drive rope is configured to be disposed in the finger part and connected with the movable part and is capable of converting a movement of the movable part into a motion of the finger part.

18 Claims, 4 Drawing Sheets

(51) Int. Cl.
*A61F 2/50* (2006.01)
*A61F 2/76* (2006.01)
*A61F 2/78* (2006.01)

(52) U.S. Cl.
CPC ............ *A61F 2002/5038* (2013.01); *A61F 2002/5093* (2013.01); *A61F 2002/587* (2013.01); *A61F 2002/7605* (2013.01); *A61F 2002/7837* (2013.01); *A61F 2002/7862* (2013.01)

(58) Field of Classification Search
CPC ...... A61F 2002/5093; A61F 2002/5087; A61F 2002/587; A61F 2002/7605; A61F 2002/7837; A61F 2002/7862
See application file for complete search history.

(56) References Cited

U.S. PATENT DOCUMENTS

| | | | |
|---|---|---|---|
| 2016/0089251 A1* | 3/2016 | Mandl | A61F 2/586 623/57 |
| 2016/0250015 A1* | 9/2016 | Kim | G01L 5/228 623/15.12 |
| 2017/0168565 A1* | 6/2017 | Cohen | A61B 5/0022 |
| 2018/0071492 A1* | 3/2018 | Laby | A61F 2/958 |

FOREIGN PATENT DOCUMENTS

| | | |
|---|---|---|
| CN | 202568539 U | 12/2012 |
| CN | 103690280 | 4/2014 |
| CN | 106963524 A | 7/2017 |
| CN | 106974749 | 7/2017 |
| CN | 108186171 | 6/2018 |
| CN | 108272537 | 7/2018 |

* cited by examiner

ARTIFICIAL LIMB

The present application claims priority to Chinese Patent Application No. 201811005799.8 filed on Aug. 30, 2018 and titled "Artificial Limb", the disclosure of which is incorporated herein by reference as part of the present application.

TECHNICAL FIELD

The embodiments of the present disclosure relate to an artificial limb.

BACKGROUND

There are many disabled people in our country. For example, the physical disabilities of the upper or lower limbs will cause great trouble to the lives of the disabled, seriously affect their normal living and working abilities. The current artificial upper limbs mainly include decorative artificial arms, rope-controlled artificial arms, myoelectric artificial arms, etc. Although the decorative artificial arms are beautiful, they has no finger sections, cannot realize grasp strength perception and grasp strength control, and lack practicality. The finger sections of the cable-controlled artificial arm and the myoelectric artificial arm mostly perform single synchronized motion, which differ greatly from the real human hand motion, and cannot meet the daily requirements and the psychological satisfaction of the user. In addition, since the shapes of the remaining limb portion of users are different, the existing arm sleeves has poor adaptabilities, which often cause wearing discomfort. Even with the custom-made prosthetic sleeves employing online modeling technologies, the obtained prosthetic sleeves are expensive, have large technical difficulty and complex production process, and thus currently cannot be universally popularized.

SUMMARY

At least an embodiment of the present disclosure provides an artificial limb, which comprises a finger part and a drive unit for the finger part, wherein
the drive unit comprises:
 a drive output part;
 a movable part, wherein the movable part is configured to be connected with the drive output part and is capable of moving under a drive of the drive output part; and
 a drive rope, wherein the drive rope is configured to be disposed in the finger part and connected with the movable part and is capable of converting a movement of the movable part into a motion of the finger part.

According to some embodiments of the present disclosure, the artificial limb may further comprise a body part, wherein
 the finger part comprises a rotary joint;
 the rotary joint is configured to be pivotally connected with the body part; and
 the drive rope of the drive unit is configured to be connected with the rotary joint so as to convert the movement of the movable part of the drive unit into a rotary motion of the finger part relative to the body part.

In the artificial limb according to some embodiments of the present disclosure, the finger part comprises at least two pivotally connected finger sections, and
 an end of the drive rope is configured to be connected with a far finger section of the at least two finger sections, the far finger section is far away from the movable part, and a remaining end of the drive rope is configured to be connected with the movable part, so that the drive rope converts the movement of the movable part into a bending motion between the at least two finger sections of the finger part.

In the artificial limb according to some embodiments of the present disclosure, the finger part further comprises a guide element, and the drive rope is configured to be arranged around the guide element.

In the artificial limb according to some embodiments of the present disclosure, the drive unit further comprises a reset element, and
 the reset element is elastic and is configured to allow the finger part to be restored to an initial state under an action of elasticity.

In some embodiments of the present disclosure, the reset element comprises an elastic rope, and the elastic rope is configured to be disposed in the finger part and arranged in parallel to the drive rope.

In the artificial limb according to some embodiments of the present disclosure, the drive output part comprises a rotary motor or a linear motor.

In the artificial limb according to some embodiments of the present disclosure, the drive output part is a rotary motor, the drive unit further comprises a lead screw, the movable part is configured to be disposed on the lead screw, and
 the lead screw is configured to rotate under a drive of the rotary motor, so that the movable part moves along the lead screw.

In the artificial limb according to some embodiments of the present disclosure, the movable part comprises a nut slider.

In the artificial limb according to some embodiments of the present disclosure, the drive unit further comprises a guide element, the guide element is configured to be arranged in parallel to the lead screw, and the movable part is configured to move on the lead screw along the guide element.

In the artificial limb according to some embodiments of the present disclosure, the movable part comprises a rolling bearing, and the rolling bearing is configured to make a rolling contact with a guide surface of the guide element.

In the artificial limb according to some embodiments of the present disclosure, the drive unit further comprises position switches disposed at two ends of the lead screw, and
 the rotary motor is configured to stop rotating in a case where the movable part contacts the position switch.

In some embodiments of the present disclosure, the artificial limb comprises a plurality of finger parts and a plurality of drive units respectively used for the plurality of finger parts, and
 the plurality of drive units are configured to be arranged in at least two layers.

In the artificial limb according to some embodiments of the present disclosure, the plurality of finger parts comprise a thumb part and at least one selected from a group consisting of a forefinger part, a middle finger part, a ring finger part or a little finger part,
 the drive unit for the thumb part and the drive unit for the at least one selected from the group consisting of the forefinger part, the middle finger part, the ring finger part or the little finger part are configured to be arranged in different layers.

In some embodiments of the present disclosure, the artificial limb comprises a processor and a myoelectric sensor, wherein the myoelectric sensor is configured to acquire a myoelectric signal on a remaining limb of a user and transmit the acquired myoelectric signal to the processor, and the processor is configured to drive the drive output part based on the received myoelectric signals.

In some embodiments of the present disclosure, the artificial limb further comprises a sleeve part, wherein the sleeve part comprises a heat setting layer, the heat setting layer comprises an elastic material, and a low-temperature wax with a melting point of 40° C.-75° C. is disposed in the elastic material.

In the artificial limb according to some embodiments of the present disclosure, the elastic material comprises thermoplastic elastomer, rubber, polyvinyl chloride (PVC) or silica gel.

In the artificial limb according to some embodiments of the present disclosure, the sleeve part further comprises a heater, and the heater is configured to be disposed in the heat setting layer and configured to heat the low-temperature wax.

In the artificial limb according to some embodiments of the present disclosure, the heat setting layer comprises a ventilation hole.

In the artificial limb according to some embodiments of the present disclosure, the sleeve part further comprises a housing layer and a flexible lining layer, and the heat setting layer is disposed between the housing layer and the flexible lining layer.

At least an embodiment of the present disclosure provides a heat setting material, which comprises:

an elastic material, wherein a low-temperature wax with a melting point of 40° C.-75° C. is disposed in the elastic material, and a heater, configured to heat the low-temperature wax.

BRIEF DESCRIPTION OF THE DRAWINGS

In order to clearly illustrate the technical solution of the embodiments of the present disclosure, the drawings of the embodiments will be briefly described in the following; it is obvious that the described drawings are only related to some embodiments of the present disclosure and thus are not limitative of the present disclosure.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the present disclosure. Apparently, the described embodiments are just a part but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for present disclosure, are not intended to indicate any sequence, amount or importance, but distinguish various components. Also, the terms such as "a," "an," etc., are not intended to limit the amount, but indicate the existence of at least one. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

As mentioned above, although there are various types of artificial limbs on the current market, these artificial limbs cannot fully satisfy the psychological requirements of users, or the cost is high so that these artificial limbs cannot be promoted and popularized better, or these artificial limb do not have adaptive modeling arm sleeves to improve the comfort for the wearers.

At least one embodiment of the present disclosure provides an artificial limb, which comprises a finger part and a drive unit for the finger part. The drive unit includes a drive output part, a movable part and a drive rope. The movable part is configured to be connected with the drive output part and is capable of moving under the drive of the drive output part. The drive rope is configured to be disposed in the finger part and connected with the movable part, and may convert the movement of the movable part into the motion of the finger part.

Figure 1:
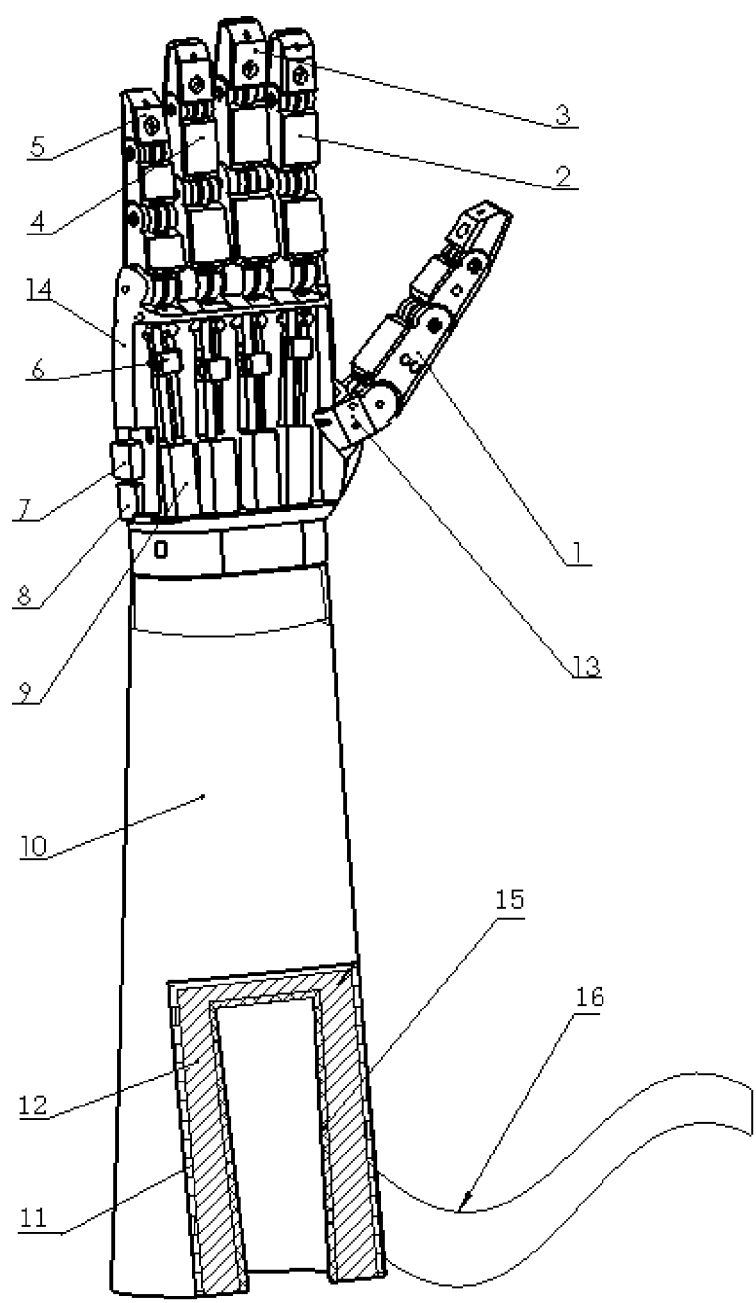
FIG. 1 is a schematic structural diagram of an artificial limb provided by at least one embodiment of the present disclosure.

FIG. 1 is a schematic structural view of an artificial limb 100 provided by at least one embodiment of the present disclosure. As shown in FIG. 1, the artificial limb 100 is the upper limb and includes at least one finger part, for instance, a plurality of finger parts, and a palm 14. The plurality of finger parts include a thumb 1, a forefinger 2, a middle finger 3, a ring ringer 4 and a little finger 5. The palm 14 is an example of the body part of the embodiments of the present disclosure. Although FIG. 1 shows that the artificial limb 100 comprises 5 fingers, it should be understood by those skilled in the art that the artificial limb 100 may include more or less fingers. For instance, the artificial limb 100 may comprise 1 finger, 2 fingers, 3 fingers, 4 fingers, 6 fingers, etc.

With reference to FIG. 1, similarly, another embodiment of the present disclosure provides an artificial limb, which is the lower limb and comprises at least one toe part, for instance, a plurality of toe parts, and a sole. The sole is an example of the body part of the embodiment of the present disclosure. It should be understood by those skilled in the art that the artificial limb may comprise more or less toes. For instance, the artificial limb may comprise 1 toe, 2 toes, 3 toes, 4 toes, 6 toes, etc.

Description will be given below to the artificial limb provided by the present disclosure by taking an artificial arm as an example. However, it should be understood by those skilled in the art that the artificial limb provided by the present disclosure is not limited thereto. For instance, the artificial limb provided by the present disclosure may also be an artificial lower limb, etc.

Figure 2:
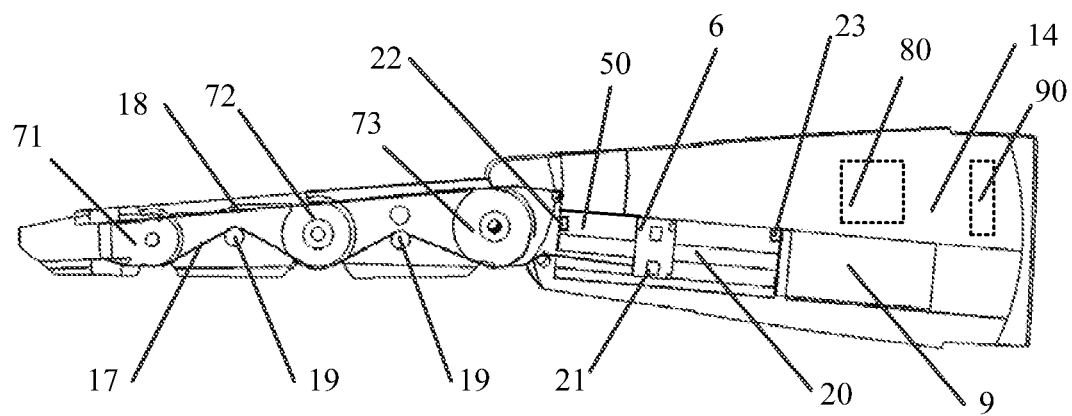
FIG. 2 is a partial sectional view of an artificial limb provided by at least one embodiment of the present disclosure.

FIG. 2 is a partial sectional view of the artificial limb 100 provided by at least one embodiment of the present disclosure. Detailed structures of the finger part and the palm 14 of the artificial limb 100 are described below with reference to FIG. 2. FIG. 2 is a partial sectional view of the finger part and the palm 14 of the artificial limb 100. The finger part in FIG. 2 may be any one of the forefinger 2, the middle finger, the ring finger 4 and the little finger 5. As shown in FIG. 2, the artificial limb 100 may further comprise a drive unit. The drive unit includes a motor 9, a nut slider 6, a drive rope 17 and a lead screw 20. The motor 9 is an example of the drive output part in the embodiments of the present disclosure, and for instance, may be a rotary motor. The lead screw 20 is connected with the motor 9 and may rotate under the drive of the motor 9. The nut slider 6 is an example of the movable part in the embodiments of the present disclosure, is connected with (for instance, in tension connection with) one end of the drive rope 17, is arranged on the lead screw 20, and is driven by the lead screw 20 to move along the lead screw 20 when the lead screw 20 rotates, so as to tighten or loosen the drive rope 17. The lead screw has self-locking characteristics, so the nut slider 6 will not move autonomously but stop at a preset position. Thus, in the case of power failure, the artificial limb 100 may still maintain the grasp action and may apply a large grasping force.

The drive rope 17 may be in various forms, e.g., nylon rope or wire rope, so the strength is high and the weight is light. For instance, the drive rope 17 may also have certain elasticity.

Although FIG. 2 shows that one drive unit is used for one finger part, it should be understood by those skilled in the art that one drive unit may also be used for a plurality of finger parts.

Although it has been shown in the present disclosure that the drive unit includes the rotary motor, the lead screw, the nut slider and the drive rope, it should be understood by those skilled in the art that in another embodiment, the drive output part and the movable part of the drive unit may also be respectively implemented as a linear motor and a slider, and the slider may move along, for instance, a guide rail, so as to tighten or loosen the drive rope. In this case, the slider is directly driven by the linear motor, so the led screw may be omitted.

In addition, it should be understood by those skilled in the art that in other embodiments, the drive unit is not limited to adopt the motor to drive the movable part and may also adopt any other appropriate forms of drive, for instance, hydraulic drive.

In the embodiment of the present disclosure, the artificial limb 100 adopts the approach of rope drive to realize the motion of the finger part, especially adopting the approach of combined motor drive and rope drive to convert the rotary motion of the motor into the movement of the nut slider 6 and subsequently convert the movement of the nut slider 6 into the motion of the finger part, thereby improving the driving force of the finger part and reducing the manufacture costs. Moreover, the safety and the maintainability of the approach of combined motor drive and rope drive are high, so the friendliness of the use process is improved.

In some embodiments of the present disclosure, the drive unit may further include a guide element, and the guide element is arranged in parallel to the lead screw and configured to guide the movement of the nut slider 6. For instance, the guide element is a guiding rail groove 50 which is arranged in parallel to the lead screw 20 and configured to limit the rotary motion of the nut slider 6 around the lead screw 20. Moreover, the nut slider 6 may move on the lead screw 20 along the extension direction of the guiding rail groove 50.

As shown in FIG. 2, in some embodiments of the present disclosure, the nut slider 6 may further include a rolling bearing 21 disposed on a surface of the nut slider 6, and the rolling bearing 21 makes rolling contact with a guide surface of the guiding rail groove 50, so as to reduce the friction of the nut slider 6 during sliding. For instance, in an example, two rolling bearings 21 may be arranged on two mutually opposite sides of the nut slider 6 and co-operate to maintain the stability of the nut slider 6 in the sliding process and reduce the friction of the nut slider 6 during sliding.

Although FIG. 2 shows that the motor 9 is arranged in the palm 14, it should be understood by those skilled in the art that the motor 9 may be arranged at any appropriate position of the artificial limb 100. For instance, the motor 9 may be also arranged in a sleeve part 10 of the artificial limb 100, and for instance, is in transmission connection with the lead screw 20 through a transmission component such as a transmission shaft (not shown).

Figure 3:
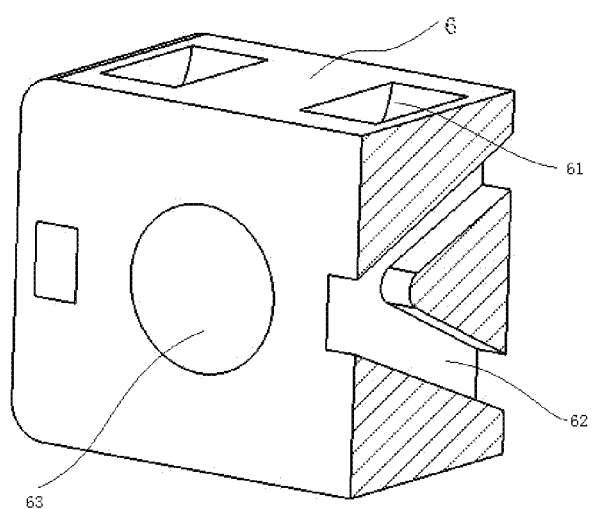
FIG. 3 is a schematic structural diagram of a nut slider of an artificial limb provided by at least one embodiment of the present disclosure.

FIG. 3 is an exemplary schematic structural diagram of the nut slider 6 of the artificial limb 100 provided by at least one embodiment of the present disclosure. As shown in FIG. 3, the nut slider 6 is substantially rectangular. The nut slider 6 includes rolling bearing support grooves 61, a V-shaped groove 62 and a lead screw hole 63. The rolling bearing support groove 61 is configured to accommodate the rolling bearing 21, so that the nut slider 6 may move along the guiding rail groove through the rolling bearing 21. Screw threads are formed on an inner wall of the lead screw hole 63, and the lead screw 20 runs through the lead screw hole 63 and is in threaded connection with the nut slider 6, so that the nut slider 6 may be arranged on the lead screw 20. The lead screw hole 63 is in thread fit with the nut slider 6. The V-shaped groove 62 is configured to fix and guide the drive rope 17. It should be understood by those skilled in the art that the structure of the nut slider 6 as shown in FIG. 3 is only illustrative, and the present disclosure is not limited thereto.

As shown in FIG. 2, the drive unit may further include position switches 22 and 23 arranged at two ends of the lead screw 20. When the nut slider 6 moves forwards (towards the left end in the figure), in the case of contacting the position switch 22, the rotor 9 stops rotating, and then the nut slider 6 stops moving forward. When the nut slider 6 moves backwards (towards the right end in the figure), in the case of contacting the position switch 23, the rotor 9 stops rotating, and then the nut slider 6 stops moving backward. In other examples of the embodiment, one ore more position switches may also be arranged at the central part (for instance, at the middle) of the lead screw 20, and when the nut slider 6 moves forwards or backwards, in the case of contacting the middle position switch, under the control of the processor (see below), the rotor 9 changes the speed, for example, speeds up or slows down, thereby speeding up or slowing down the motion of the finger. The embodiments of the present disclosure have no limitation on the type, the number and the arranging position of the position switches.

The finger part as shown in FIG. 2 includes three finger sections; adjacent finger sections in the three finger sections and the finger sections and the palm 14 are pivotally connected with each other through pivot parts 71, 72 and 73; the finger part is one of other fingers except the thumb; and the thumb generally includes two finger sections which are pivotally connected with each other through a pivot part, and the finger sections are pivotally connected with the palm 14 through a rotary joint 13 which will be described below. As shown in FIG. 2, one end of the drive rope 17 is connected with the finger section of the three finger sections which is the farthest from the nut slider 6, and the other end of the drive rope 17 is connected with the nut slider 6, so that the drive rope may convert the movement of the nut slider 6 into the bending motion among the three finger sections of the finger part. It should be understood by those skilled in the art that the finger part of the artificial limb provided by the embodiment of the present disclosure may also include more or less finger sections, for instance, 2 finger sections, 4 finger sections or 5 finger sections.

In some embodiments of the present disclosure, the finger part may also include a plurality of protruded guide shafts 19, and the drive rope 17 is arranged around the guide shafts 19. The guide shaft 19 is an example of the guide element in the present disclosure. As shown in FIG. 2, the left end of the drive rope 17 is connected with the finger section which is the farthest from the nut slider 6. In the direction from left to right, the drive rope 17 bypasses the pivot part 71 from below at first, and then is folded upwardly and bypasses one guide shaft 19, is folded downwardly and bypasses the pivot part 72, is folded upwardly and bypasses one guide shaft 19, is folded downwardly and bypasses the pivot part 73, and is finally connected to the nut slider 6. The drive rope 17 is Z-shaped in the whole travel, so as to facilitate the bending motion of the finger part. For instance, a rolling bearing may also be sleeved on the guide shaft 19, so as to reduce the friction of the drive rope 17 when sliding on a surface of the guide shaft 19. In other examples, the guide element may also be in other forms, for instance, protrusions provided with holes, and no limitation will be given here in the embodiments of the present disclosure.

In some embodiments of the present disclosure, the artificial limb 100 may further comprise a reset element, so that the bent finger part may be restored to almost the initial state, for instance, restored to the initial state. For instance, the finger part is gradually restored to the initial state along with the process of moving backwards of the nut slider 6, namely the nut slider 6 plays an opposite role to the drive rope 17. In an example, the reset element includes an elastic rope 18. As shown in the figure, the elastic rope 18 is disposed in the finger part and substantially arranged in parallel to the drive rope 17, and is extended on upper sides of the pivot parts 71, 72 and 73 among the finger sections. When the finger part is bent, the elastic rope 18 is elastically deformed (elastic stretching); and when the finger part is straightened, the elastic rope 18 elastically restores to the initial shape, and the finger part is restored to, for instance, the initial state under the action of elasticity. For instance, the elastic rope 18 allows the finger part to be restored from the bending state to the straightened state.

In another example, the reset element includes a plurality of elastic sheets (or spring sheets, not shown), and the plurality of elastic sheets are respectively disposed on the upper parts of the pivot parts 71, 72 and 73 among the finger sections. When the finger part is bent, the elastic sheet at the bending position is elastically deformed (bending deformation); and when the finger part is straightened, the elastically deformed elastic sheet is elastically restored to the initial state and allows the finger part to be restored, for instance, to the initial state under the action of elasticity.

However, it should be understood by those skilled in the art that the artificial limb 100 may also adopt any other appropriate unit to restore the finger part to the initial state. For instance, in some other embodiments of the present disclosure, the artificial limb 100 may also adopt a hydraulic rod to restore the finger part to the initial state.

As shown in FIG. 1, the artificial limb 100 provided by at least one embodiment of the present disclosure may further comprise a rotary joint 13 for connecting the thumb 1 and the palm 14. The rotary joint 13 is pivotally connected with the palm 14. The rotary joint 13 may rotate to drive the thumb 1. The drive unit of the artificial limb 100 provided by at least one embodiment of the present disclosure may include a first drive unit for driving the finger sections of the finger part to bend and a second drive unit for driving the rotary joint. For instance, apart from the drive unit (the first drive unit) for driving the finger sections of the thumb to bend, the artificial limb 100 further comprises a drive unit (the second drive unit) for driving the rotary joint 13 of the thumb. The drive rope of the second drive unit for the driving the rotary joint 13 is connected with the rotary joint 13. The second drive unit for driving the rotary joint 13 may be the same or different from the above first drive unit. The second drive unit for the rotary joint 13 may adopt any appropriate form, for instance, may include a rotary motor, a lead screw, a nut slider and a drive rope, or may include a linear motor, a slider and a drive rope.

Although FIG. 1 only shows that the thumb 1 includes the rotary joint 13, it should be understood by those skilled in the art that other fingers (for example, the forefinger 2, the middle finger 3, the ring finger 4 and/or the little finger 5) may also include the rotary joint, and the rotary joints connect these fingers with the palm 14. No limitation will be given here in the present disclosure. In this case, the pivot part 73 of other fingers as shown in FIG. 2 is replaced by the rotary joint or pivotally connected with the rotary joint, and the second drive unit may also be provided for the rotary joint of other fingers. Or, moreover, in certain embodiment, certain finger (for instance, the thumb) may be only provided with the rotary joint and the second drive unit but not provided with the finger sections for the bending (holding) motion and the corresponding first drive unit. By adoption of the rotary joint 13 and the second drive unit for the rotary joint 13, the lateral motion of the finger (especially the thumb) may be realized, so the degree of personification is high, thereby meeting the requirements needs and the psychological satisfaction of users.

Figure 4:
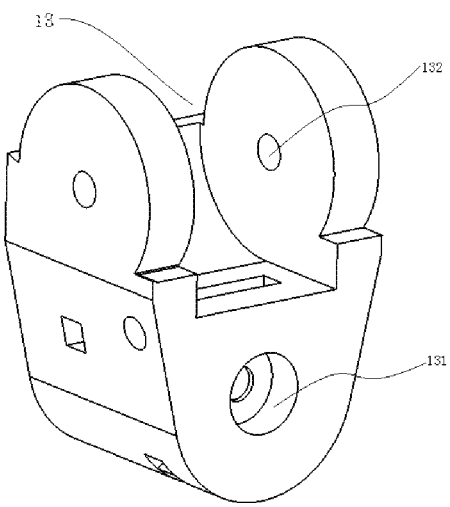
FIG. 4 is a schematic structural diagram of a rotary joint of an artificial limb provided by at least one embodiment of the present disclosure.

FIG. 4 is an exemplary schematic structural diagram of the rotary joint 13 of the artificial limb 100 provided by at least one embodiment of the present disclosure. As shown in FIG. 4, the rotary joint 13 includes a first shaft hole 131 and a second shaft hole 132. The rotary joint 13 may rotate relative to the palm 14 around a rotary shaft passing through the first shaft hole 131. The finger sections may rotate relative to the rotary joint 13 around a rotary shaft passing through the second shaft hole 132. The first shaft hole 131 is substantially perpendicular to the second shaft hole 132. A part of the rotary joint 13 connected with the palm 14 and/or a part of the rotary joint 13 connected with the finger section is curved, so as to reduce friction. It should be understood by those skilled in the art that the structure of the rotary joint 13 as shown in FIG. 4 is only illustrative, and no limitation will be given here in the present disclosure.

Figure 5:
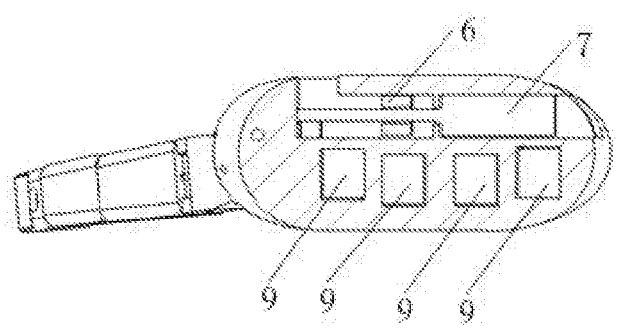
FIG. 5 is a rear view of a palm of an artificial limb provided by at least one embodiment of the present disclosure.

FIG. 5 is a rear view of the palm 14 of the artificial limb 100 provided by at least one embodiment of the present disclosure. In FIG. 5, four motors 9 are respectively motors of the drive units of the forefinger 2, the middle finger 3, the ring finger 4 and the little finger 5, and a motor 7 is a motor of the drive unit of the rotary joint 13 of the thumb 1. As shown in FIG. 5, the drive units for the forefinger 2, the middle finger 3, the ring finger 4 and the little finger 5 are substantially arranged in the same layer, and the drive unit for the thumb 1 is substantially arranged in another layer. Thus, the drive units for the forefinger 2, the middle finger 3, the ring finger 4 and the little finger 5 and the drive unit for the thumb 1 are respectively arranged in two layers.

Although FIG. 5 shows that the drive units in the artificial limb 100 are arranged in two layers, it should be understood by those skilled in the art that the drive units may also be arranged in more layers. For instance, the drive units for the forefinger 2, the middle finger 3, the ring finger 4 and the little finger 5 are substantially arranged in a first layer; the second drive unit for the rotary joint 13 of the thumb 1 is arranged in a second layer; and the first drive unit for the bending motion of the finger sections of the thumb 1 is arranged in a third layer. Or, the drive units are arranged in more layers, which may be determined according to the factors such as the size of the drive unit and the thickness of the palm. The drive units do not interfere with each other by arrangement of the drive units in a plurality of layers.

The movement direction of the nut slider 6 driven by the motor 7 is substantially perpendicular to the movement direction of the nut slider driven by the motor 9. The motor 7 in FIG. 5 may also be a motor 8 of the drive unit for the finger sections of the thumb 1. Although FIG. 1 shows that the motor 7 is closer to the finger part compared with the motor 8, it should be understood by those skilled in the art that the motor 8 may also be closer to the finger part compared with the motor 7, and no limitation will be given here in the present disclosure.

In some embodiments of the present disclosure, as shown in FIG. 2, the artificial limb 100 may further comprise a processor 80 and a myoelectric sensor 90 in signal connection with the processor 80. The signal connection may be a wired or wireless connection. The myoelectric sensor 90 is configured to acquire myoelectric signals on the remaining limb of the user and transmits the acquired myoelectric signals to the processor 80, and the processor 80 is configured to control the motor 9, the motor 8 and/or the motor 7 in the drive unit on the basis of the received myoelectric signals. The user may actively control the artificial limb and good interactivity is provided by the arrangement of the myoelectric sensor 90 and the processor 80.

Description will be given below to the processing process of the processor 80 and the myoelectric sensor 90 by taking the case where the artificial limb 100 is an artificial arm as an example. In the example, the myoelectric sensor 90 may adopt one of the following forms. One myoelectric sensor is of a form similar to the wrist strap and directly sleeved on the arm. Another myoelectric sensor is provided with three electrode patches which are respectively attached to a position slightly above the elbow of the arm and the inner and outer sides of the forearm. The myoelectric sensor includes three wires which are respectively connected to an anode, a grounding port (a controller provides 5V voltage) and an analog read interface for reading the analog voltage of the sensor, of the processor. When the brain sends a signal to grasp something after the user wears the artificial arm 100, the nerves of the arm send out corresponding signals that drive muscles to work (contraction or relaxation), thereby applying forces with corresponding muscles. At this point, the myoelectric sensor 90 is adopted to detect that the analog voltage of the myoelectric signal produced by the current muscle action is higher than the analog voltage under the resting condition. The processor 80 reads the analog voltage through the analog read interface and continuously compares the read analog voltage with the analog voltage at the previous moment, determines that there is a grasp signal when detecting an increase in the analog voltage, and then sends a drive signal to the motor through an output port. In the embodiment of the present disclosure, the processor 80 may be any unit with data processing capability, for instance, a central processing unit (CPU), a digital signal processor (DSP), a microcontroller or an embedded processor.

Description will be given below to the grasp action and the reset action of the finger when the artificial limb 100 provided by at least one embodiment of the present disclosure is an artificial arm with reference to FIG. 2.

The myoelectric sensor 90 acquires the myoelectric signals on the arm of the user first, and then the processor 80 receives the myoelectric signals and sends a control signal to the motor 9 and/or the motor 8 according to the determination of the received myoelectric signals; the motor 9 and/or the motor 8 drives the lead screw 20 to rotate forwards; the nut slider 6 cooperates with the lead screw 20; and when the lead screw 20 rotates, as there is the guiding rail groove of the nut slider 6 on the inside of the palm 14, the rotation of the nut slider 6 may be limited, so the rotary motion of the lead screw 20 may be converted into the linear motion of the nut slider 6. The nut slider 6 moves backwards and drives the drive rope 17 of which one end is fixed on the finger section at the far end to move backwards; and until the nut slider 6 touches the position switch 23, the processor 80 controls the motor 9 and/or the motor 8 to stop moving, thereby completing the grasp action of the artificial limb 100. The guide shaft 19 of the drive rope 17 is disposed in both the middle finger section and the near finger section of the finger, so the entire finger may produce bending motion, thereby realizing the hand-like enveloping grasp action.

When the artificial limb 100 reaches the stable grasp state and the myoelectric sensor 90 detects the myoelectric signal of a corresponding release action on the arm of the user, the processor 80 sends a control signal to the motor 9 and/or the motor 8, and the motor 9 and/or the motor 8 rotates reversely; at this point, the nut slider 6 slides forwards due to the limitation of the guiding rail groove 50 and drives the drive rope 17 to be in relaxed state; at this point, under the action of the elastic force of the elastic rope 18, the finger is gradually restored to the initial state; and until the nut slider 6 touches the position switch 22, the processor controls the motor 9 and/or the motor 8 to stop moving, and the reset action of the artificial limb is completed.

Description will be given below to the lateral motion of the thumb 1 of the artificial limb 100 provided by at least one embodiment of the present disclosure with reference to FIG. 1. The myoelectric sensor 90 acquires myoelectric signals on the arm first, and then the processor 80 receives the myoelectric signals and sends a control signal to the motor 7 according to the determination of the received myoelectric signals; the motor 7 drives the lead screw 20 to rotate forward; the nut slider 6 cooperates with the lead screw 20; and when the lead screw 20 rotates, as there is the guiding rail groove 50 of the nut slider 6 on the inside of the palm 14, the rotation of the nut slider 6 may be limited, so the rotary motion of the lead screw 20 is converted into the linear motion of the nut slider 6. The nut slider 6 moves backwards and then drives the drive rope 17 of which one end is fixed on the rotary joint 13 to move backwards; and until the nut slider 6 touches the position switch 23, the processor 80 controls the motor 7 to stop moving. The reset action of the thumb 1 restoring from the lateral motion position to the initial position (for instance, a position where the thumb 1 leans against the palm 14) is similar to the reset action of the finger, the detailed description of which will be omitted.

In addition, it should be understood by those skilled in the art that the artificial limb 100 provided by at least one embodiment of the present disclosure may also not comprise the myoelectric sensor 90 but directly adopts the processor 80 to generate signals for controlling the motor 7, the motor 8 and/or the motor 9.

Some embodiments of the present disclosure further provide a sleeve part for the artificial limb, which is connected with the remaining limb of the user, and the remaining limb of the user is inserted into the sleeve part. The sleeve part comprises a heat setting portion. The heat setting portion includes elastic materials and a heater. Low-temperature wax with a melting point of 40° C.-75° C. is disposed in the elastic material. The heater is configured to heat the low-temperature wax, so as to mold the elastic materials. The sleeve part may be applied to different types of artificial limbs, but is not limited to the above-mentioned artificial limbs. Moreover, for instance, the melting point of the low-temperature wax is 50° C.-70° C., so the heat setting portion may have better stability in daily use.

For instance, in the embodiment as shown in FIG. 1, the artificial limb 100 may further comprise a sleeve part 10. The sleeve part 10 is an example of the above sleeve part. The sleeve part 10 includes a housing layer 11, a heat setting layer 12 and a flexible lining layer 15.

In some embodiments of the present disclosure, the housing layer 11 may be formed by means of 3D printing, so the manufacturing process is simple and the shape is realistic, and a ratio of 1:1 to the real human hand may be realized. In some other embodiments of the present disclosure, the housing layer 11 may also be formed by injection molding. The housing layer 11 may be formed by, for instance, metal, leather, silica gel, polyethylene, polypropylene, polyester or ethylene-vinyl acetate (EVA) copolymer.

Figure 6:
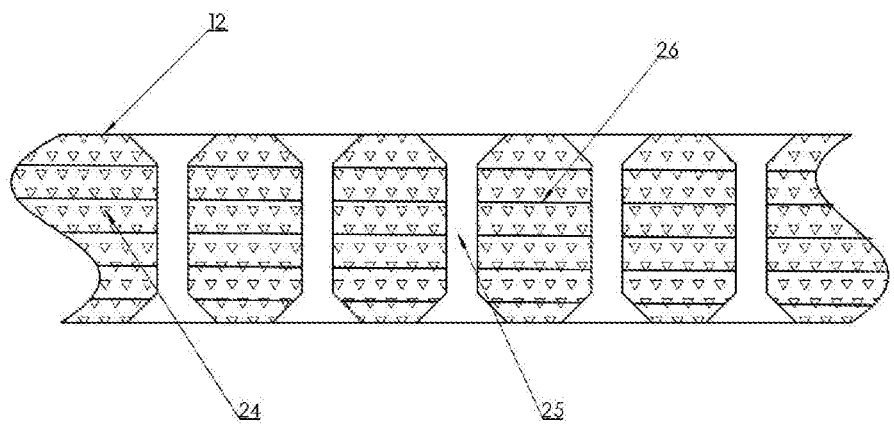
FIG. 6 is a schematic structural diagram of a heat setting layer of an artificial limb provided by at least one embodiment of the present disclosure.

FIG. 6 is a schematic structural diagram of the heat setting layer 12 of the artificial limb 100 provided by at least one embodiment of the present disclosure. As shown in FIG. 6, the heat setting layer 12 includes elastic materials. Low-temperature wax 24 is disposed in the elastic material. For instance, the melting point of the low-temperature wax 24 is 40° C.-75° C. The elastic materials of the heat setting layer 12 may include but is not limited to thermoplastic elastomer, rubber, polyvinyl chloride (PVC) or silica gel.

The heat setting layer 12 may further include resistance wires 26 and ventilation holes 25. The resistance wires 26 may generate heat to heat the low-temperature wax 24 when energized. It should be understood by those skilled in the art that other elements capable of generating heat, for instance, an electric heating film or a microwave heat source may also be adopted to replace the resistance wires 26. The arrangement of the resistance wires 26 in the heat setting layer 12 may make the heating of the low-temperature wax 24 quickly and conveniently.

However, it should be also understood by those skilled in the art that the heat setting layer 12 may also not include the resistance wires 26. In the process of using the artificial limb 100, an external heat source may be used to heat the low-temperature wax 24.

The ventilation holes 25 are distributed in the heat setting layer 12, so that the sleeve part 10 may have ventilation characteristics. In some embodiments of the present disclosure, the ventilation holes 25 are uniformly distributed in the heat setting layer 12. In some other embodiments of the present disclosure, the ventilation holes 25 are only distributed in one part of the heat setting layer 12. In some embodiments of the present disclosure, the housing layer 11 and the flexible lining layer 15 may also include ventilation holes at positions corresponding to the ventilation holes 25, so that the sleeve part 10 may have good ventilation characteristics.

The low-temperature wax 24 in the heat setting layer 12 is in a solid state at room temperature (for example, a room temperature of 25° C.). When the user wears the artificial limb for the first time, the resistance wire 26 is electrified first, so the low-temperature wax 24 may reach the melting point. After the low-temperature wax 24 reaches the melting point, the low-temperature wax is converted from solid to liquid that may flow. At this point, the user inserts the remaining limb into the sleeve part 10. As the low-temperature wax 24 has become liquid at this point, the heat setting layer 12 may form receiving cavities with different shapes according to the shapes of the artificial limbs of the users. After the formed receiving cavity is stabilized, the temperature of the sleeve part 10 may be lowered from the outside. As the ventilation holes 25 are uniformly distributed on the heat setting layer 12, the receiving cavities based on different shapes of the remaining limbs may be rapidly manufactured. The receiving cavity and the remaining limb have a high fitting degree, which makes the user feel more comfortable.

The heat setting layer 12 is disposed between the housing layer 11 and the flexible lining layer 15. The flexible lining layer 15 may be made from leather, woven fabric, silica gel or the like to provide a comfortable wearing feeling.

It should be understood by those skilled in the art that although FIG. 1 shows that the sleeve part 10 includes the housing layer 11, the heat setting layer 12 and the flexible lining layer 15, one or both of the housing layer 11 and the flexible lining layer 15 may be omitted, and no limitation will be given here in the present disclosure. In some embodiments of the present disclosure, the sleeve part 10 may also include an adhesive layer to bond the housing layer 11, the heat setting layer 12 and the flexible lining layer 15.

In some embodiments of the present disclosure, the artificial limb 100 may further comprise a fixing strap 16 which is disposed on the outside of the sleeve part 10 and configured to circumferentially fix the sleeve part 10, thereby firmly fixing the sleeve part 10 and the remaining limb of the user. For instance, the fixing strap 16 may be a hook-and-loop fastener.

The artificial limb provided by at least one embodiment of the present disclosure may meet the psychological requirements of the user. Moreover, the manufacture costs of the artificial limb provided by at least one embodiment of the present disclosure are low and thus the artificial limb provided by at least one embodiment of the present disclosure may be better prompted and popularized. Furthermore, the artificial limb provided by at least one embodiment has an arm sleeve that achieves self-adaptive modeling to improve the comfort for the wearer.

Although the present disclosure has been described in detail with reference to the general and particular embodiments, modifications or improvements may be made to the disclosed embodiments, which will be apparent to those skilled in the art. Therefore, such modifications or improvements made without departing from the spirit of the present disclosure are intended to fall within the scope of the present disclosure.

The foregoing merely are exemplary embodiments of the disclosure, and not intended to define the scope of the disclosure, and the scope of the disclosure is determined by the appended claims.

What is claimed is:

1. An artificial limb, comprising a finger part and a drive unit for the finger part, wherein
the drive unit comprises:
a drive output part;
a movable part, wherein the movable part is configured to be connected with the drive output part and is capable of moving under a drive of the drive output part;
a drive rope, wherein the drive rope is configured to be disposed in the finger part and connected with the movable part and is capable of converting a movement of the movable part into a motion of the finger part;
wherein the drive unit further comprises a reset element, and the reset element is elastic and is configured to allow the finger part to be restored to an initial state under an action of elasticity;
the reset element comprises an elastic rope, and the elastic rope is configured to be disposed in the finger part and arranged in parallel to the drive rope; and
the finger part comprises at least two finger sections and at least one pivot part, wherein adjacent finger sections in the at least two finger sections are pivotally connected with each other through the pivot part, the drive rope bypasses the pivot part from below, and the elastic rope extends on the pivot part.

2. The artificial limb according to claim 1, further comprising a body part, wherein
the finger part comprises a rotary joint,
the rotary joint is configured to be pivotally connected with the body part, and
the drive rope of the drive unit is configured to be connected with the rotary joint so as to convert the movement of the movable part of the drive unit into a rotary motion of the finger part relative to the body part.

3. The artificial limb according to claim 1, wherein the finger part comprises at least two pivotally connected finger sections, and
an end of the drive rope is configured to be connected with a far finger section of the at least two finger sections, the far finger section is far away from the movable part, and a remaining end of the drive rope is configured to be connected with the movable part, so that the drive rope converts the movement of the movable part into a bending motion between the at least two finger sections of the finger part.

4. The artificial limb according to claim 3, wherein the finger part further comprises a guide element, and
the drive rope is configured to be arranged around the guide element.

5. The artificial limb according to claim 1, wherein the drive output part comprises a rotary motor or a linear motor.

6. The artificial limb according to claim 5, wherein the drive output part is a rotary motor; the drive unit further comprises a lead screw, the movable part is configured to be disposed on the lead screw, and
the lead screw is configured to rotate under a drive of the rotary motor, so that the movable part moves along the lead screw.

7. The artificial limb according to claim 6, wherein the movable part comprises a nut slider.

8. The artificial limb according to claim 6, wherein the drive unit further comprises a guide element, the guide element is configured to be arranged in parallel to the lead screw, and the movable part is configured to move on the lead screw along the guide element.

9. The artificial limb according to claim 8, wherein the movable part comprises a rolling bearing, and
the rolling bearing is configured to make a rolling contact with a guide surface of the guide element.

10. The artificial limb according to claim 6, wherein the drive unit further comprises position switches disposed at two ends of the lead screw, and
the rotary motor is configured to stop rotating in a case where the movable part contacts the position switch.

11. The artificial limb according to claim 1, wherein the artificial limb comprises: a plurality of finger parts and a plurality of drive units respectively used for the plurality of finger parts, and
the plurality of drive units are configured to be arranged in at least two layers.

12. The artificial limb according to claim 11, wherein the plurality of finger parts comprise a thumb part and at least one selected from a group consisting of a forefinger part, a middle finger part, a ring finger part or a little finger part,
the drive unit for the thumb part and the drive unit for the at least one selected from the group consisting of the forefinger part, the middle finger part, the ring finger part or the little finger part are configured to be arranged in different layers.

13. The artificial limb according to claim 1, further comprising a processor and a myoelectric sensor, wherein
the myoelectric sensor is configured to acquire a myoelectric signal on a remaining limb of a user and transmit the acquired myoelectric signal to the processor, and
the processor is configured to drive the drive output part based on the received myoelectric signals.

14. The artificial limb according to claim 1, further comprising a sleeve part, wherein the sleeve part comprises a heat setting layer,
the heat setting layer comprises an elastic material, and a low-temperature wax with a melting point of 40° C.-75° C. is disposed in the elastic material.

15. The artificial limb according to claim 14, wherein the elastic material comprises thermoplastic elastomer, rubber, polyvinyl chloride (PVC) or silica gel.

16. The artificial limb according to claim 14, wherein the sleeve part further comprises a heater; and
the heater is configured to be disposed in the heat setting layer and configured to heat the low-temperature wax.

17. The artificial limb according to claim 14, wherein the heat setting layer comprises a ventilation hole.

18. The artificial limb according to claim 14, wherein the sleeve part further comprises a housing layer and a flexible lining layer, and the heat setting layer is disposed between the housing layer and the flexible lining layer.

* * * * *